United States Patent [19]
Danks

[11] Patent Number: 5,868,714
[45] Date of Patent: Feb. 9, 1999

[54] TROCAR REDUCER SYSTEM

[75] Inventor: John K. Danks, Delray Beach, Fla.

[73] Assignee: Endoscopic Concepts, Inc., Delray Beach, Fla.

[21] Appl. No.: 714,765

[22] Filed: Sep. 16, 1996

[51] Int. Cl.⁶ .................................................. A61M 5/00
[52] U.S. Cl. ...................... 604/256; 604/167; 604/264; 215/296; 220/789
[58] Field of Search ................................ 604/246, 19, 21, 604/22, 27, 29, 35, 36, 43–45, 51, 54, 115, 164, 167, 169, 187, 239, 264, 256, 280; 215/355, 296; 220/DIG. 19, 789, 791, 800

[56] References Cited

U.S. PATENT DOCUMENTS

| | | | |
|---|---|---|---|
| 5,104,383 | 4/1992 | Shichman | 604/167 |
| 5,263,944 | 11/1993 | Vidal et al. | 604/256 |
| 5,338,307 | 8/1994 | Stephens et al. | 604/167 |
| 5,385,560 | 1/1995 | Wolf | 604/264 |
| 5,460,615 | 10/1995 | Storz | 604/167 |
| 5,569,206 | 10/1996 | Gorman, Jr. et al. | 604/167 |
| 5,607,397 | 3/1997 | Stephens et al. | 604/167 |
| 5,611,792 | 3/1997 | Gustafsson | 604/403 |

OTHER PUBLICATIONS

AutoSuture Disposable Surgiport Converter Instructions for Use by USSC © 1989.
Ethicon, Inc. Endopath Multiseal Cap Instructions for Use © 1993.

*Primary Examiner*—Corrine M. McDermott
*Assistant Examiner*—Cris L. Rodriguez
*Attorney, Agent, or Firm*—Miller & Martin

[57] ABSTRACT

A novel reducer system is provided for a trocar cannula. The reducer system fastens to the cannula end and a living hinge allows a reducer cap to be closed over the cannula lumen to allow the cannula to be used with smaller diameter surgical instruments. By fastening the reducer system to the exterior of the cannula end, the system can be placed in position on the cannula prior to surgery, even while a large diameter obturator is used with the cannula.

16 Claims, 3 Drawing Sheets

TROCAR REDUCER SYSTEM

BACKGROUND OF THE INVENTION

This invention relates to a surgical instrument commonly referred to as a trocar, or an obturator and cannula, often used in laparoscopic or arthroscopic surgery. More particularly, the invention relates to a reducer cap used in conjunction with a trocar cannula.

Many surgical procedures are now being performed with the use of trocars and cannulas. Originally these devices were used for making a puncture and leaving a tube to drain fluids. As technology and surgical techniques have advanced, it is now possible to insert surgical instruments through the cannulas and perform invasive procedures through openings less than half an inch in diameter. Previously these procedures required incisions of many inches. By minimizing the incision, stress, and loss of blood, the patients recovery times are dramatically reduced.

Surgical trocars are most commonly used in laparoscopic surgery. Prior to use of the trocar, the surgeon will usually introduce a Veress needle into the patient's abdominal cavity. The Veress needle has a stylet which permits the introduction of gas into the abdominal cavity. After the Veress needle is properly inserted, it is connected to a gas source and the abdominal cavity is insufflated to an approximate abdominal pressure of 15 mm Hg. By insufflating the abdominal cavity, pneumoperitoneum is created separating the wall of the body cavity from the internal organs.

A trocar is then used to puncture the body cavity. The piercing tip or obturator of the trocar is inserted through the cannula or sheath, and the cannula partially enters the body cavity through the incision made by the trocar. The obturator can then be removed from the cannula and an elongated endoscope or camera may be inserted through the cannula to view the body cavity. Surgical instruments may also be inserted to perform ligations or other procedures.

Once the cannula has been introduced into the opening in the body cavity wall, the pneumoperitoneum may be maintained by introducing gas into the abdominal cavity through the cannula. Various seals and valves have been utilized to allow abdominal pressure to be maintained in this fashion. Maintaining abdominal pressure is important both to allow working room in the body cavity for instruments introduced through the cannula, and to provide free space for the puncturing of the body cavity wall by one or more additional trocars as may be required for some procedures.

Endoscopic surgical procedures often require the use of surgical tools of varying diameters. Although trocars are provided in different diameters, some procedures will inevitably require the use of surgical tools with smaller diameters than that of the cannula. Converting the cannula's diameter rather than inserting separate cannulas for different surgical tool sizes reduces recovery time and the risk of surgical accidents. Where the diameter of the cannula must be converted to use smaller diameter tools, pneumoperitoneum must be maintained while converting the proximate opening of the cannula from a larger diameter to a smaller one. To maintain pneumoperitoneum during surgery, an airtight seal must be made around the smaller diameter surgical tools inserted into the larger diameter cannula.

A system which rapidly and efficiently reduces the diameter of the cannula while retaining pneumoperitoneum is necessary during endoscopic surgical procedures. Reducing systems are described in Stephens, U.S. Pat. No. 5,338,307; Wulf, U.S. Pat. No. 5,385,560; and Shichman, U.S. Pat. No. 5,104,383.

Reducer systems currently on the market consist either of a plate which must be slid into place or a cap which snaps onto the cannula housing. For instance, Shichman, U.S. Pat. No. 5,104,383, shows a sliding plate reducer system. This reducer system cannot be attached to the cannula before surgery, but only after the cannula has been inserted through the abdominal cavity wall and the obturator removed. This reducer system requires the surgeon to slide the plate on for smaller instruments used and back off to return to the original diameter of the cannula. Since the plate is not attached to the cannula, the diameter cannot be reduced as efficiently since the plate must be searched for during surgery.

Another system, described in Stephens, U.S. Pat. No. 5,338,307, consists of a reducer cap which snaps onto the cannula housing. This system consists of a base which attaches to the cannula housing, and a cap, containing a gasket assembly, which is attached to the reducer system base by a pin and hinge assembly. The cap is designed so surgeons can flip the cap to convert from one diameter size to another. Although this system does remain attached to the cannula during surgery, several disadvantages exist with Ethicon's reducer cap. For instance, because the cap latches to the base of the reducer system base, if the latch fails to release the surgeon may inadvertently remove the entire reducer system with attendant loss of pneumoperitoneum. Most significantly, this reducer system base attaches to the cannula using the same slots in the cannula that engage tabs from the obturator when the trocar is assembled for piercing the body cavity wall. The reducer cap can only be mounted in place after the incision is made and the obturator removed from the cannula.

Finally, with the current emphasis on cost controls in health care, the most cost efficient product should be utilized whenever possible. The pin and hinge assembly of Stephens, connecting the base and the cap entails higher costs due to the specially molded pieces and increased labor required to assemble the cap to the base. Therefore, a need exists for an attachable, cost efficient trocar reducer system which can be easily used while reducing the risk of mishandling the system during laparoscopic and similar surgical procedures.

SUMMARY OF THE INVENTION

Accordingly, it is the primary object of the invention to provide a safer and more efficient reducer system for a trocar cannula.

It is also an object of the invention to provide a fast, efficient method of converting from a larger diameter to a smaller diameter and vice versa which can easily be accomplished by opening or closing a reducer cap with a finger.

It is a further object of the invention to provide a cost effective reducer system by utilizing a living hinge which requires fewer parts and less labor to assemble.

It is yet a further object of the invention to provide a trocar reducer system that can be secured to the cannula before surgery commences and easily moved into place when needed.

Accordingly, the trocar reducer system consists of a fastener ring and the reducer cap which contains the gasket assembly. The fastener ring snaps into place over the raised edge at the distal end of Endoscopic Concept's cannula end cap. The fastener ring consists of flexible plastic in the shape of a circular ring with a fastener ring removal tab to be used as a handle to remove the reducer system from the cannula end cap. Integrally attached to the fastener ring is the reducer cap containing the gasket assembly. The fastener ring and the cap are connected by a living hinge which consists of a thin sheet of plastic with a bend in the middle. This living hinge is molded of the same piece of plastic as the fastener ring and cap. The advantage of a living hinge is the requirement of few raw materials and no labor to assemble the fastener ring and cap. Another advantage of the living hinge is its flexibility which allows the cap to be opened and closed with minimal effort, such as the flip of a finger.

The reducer cap contains the gasket assembly. The gasket assembly consists of the reducer cap wiper seal attached to the gasket. The gasket is designed so that when the cap is closed and a smaller diameter surgical tool inserted into the cannula, an airtight seal will be formed at the cannula handle end.

The reducer cap preferably snaps closed into place on the raised edge at the proximate end of the cannula end cap. Since the reducer cap attaches to the cannula end cap and not the base or fastener ring of reducer system itself, the probability of inadvertently removing the reducer system when converting from a smaller diameter to the normal diameter of the cannula is greatly reduced. The design of this reducer system allows for the quick, efficient conversion of a larger diameter cannula for use with smaller diameter surgical tools without losing pneumoperitoneum.

BRIEF DESCRIPTIONS OF THE DRAWINGS

DESCRIPTION OF THE PREFERRED EMBODIMENTS

Figure 1A:
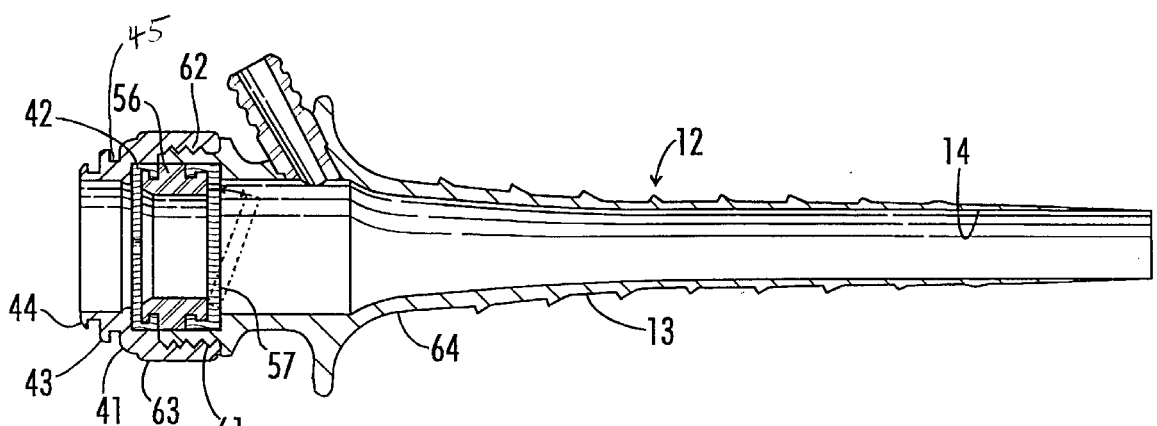
FIG. 1A is a cross sectional side view of a cannula with a an end cap.
Figure 1B:
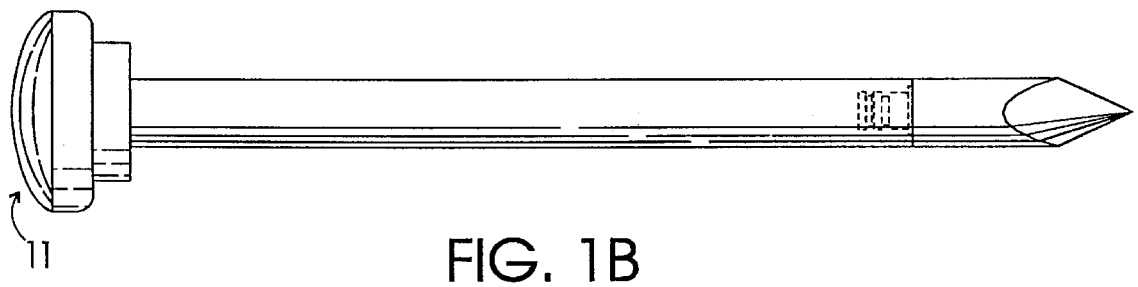
FIG. 1B is a side view of a conventional obturator which is adapted for use with the cannula of FIG. 1A.

A reducer system 21 to be used with a trocar is shown in FIGS. 2, 4, 5, and 6. The invention commonly known as a trocar is comprised of two major components. These are a cannula 12, shown in FIG. 1A, and an obturator 11, shown in FIG. 1B. The obturator 11 and cannula 12 are interfitting and are used together to penetrate a body cavity wall. Once the body cavity wall is penetrated, the obturator 11 may be removed and other medical instruments may be introduced into a lumen 14 of the cannula 12. Male threads 61, located at the proximate end 64 of the illustrated cannula tube 13, allow the cannula tube 13 to be securely coupled with an end section such as cap 41, which contains corresponding female threads 62. The end cap 41 also contains an aperture 51 to permit insertion of an obturator 11 or other surgical instruments, and gripping protrusions 63 used to facilitate fastening and unfastening the cap 41.

Figure 2:
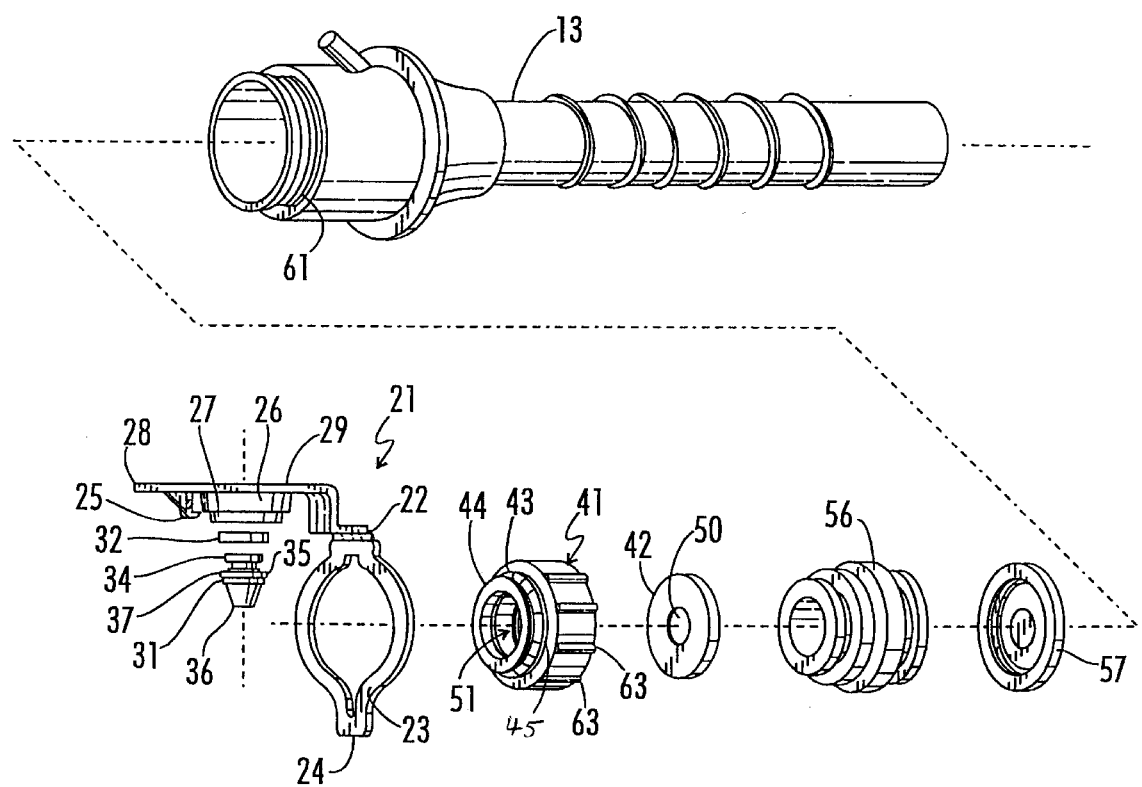
FIG. 2 is an exploded perspective view of the cannula of FIG. 1A and the trocar reducer system.
Figure 3A:
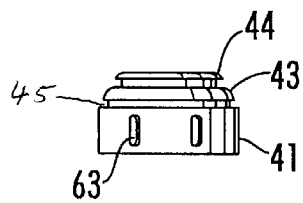
FIG. 3A is a side view of the end cap of the cannula of FIG. 1A in isolation.
Figure 3B:
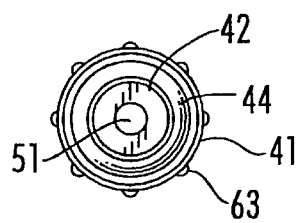
FIG. 3B is an end view of the end cap of the cannula of FIG. 1A.
Figure 3C:
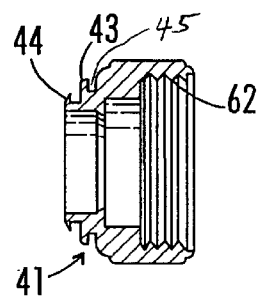
FIG. 3C is a cross sectional side view of the end cap of the cannula of FIG. 1A in isolation.
Figure 4:
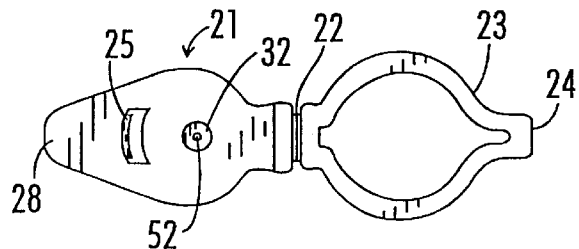
FIG. 4 is a top view of the trocar reducer system of FIG. 2 in isolation.

As shown in FIGS. 2 and 4, the reducer system 21 contains a fastener such as fastener ring 23 which fastens the reducer system 21 to the end cap 41. The illustrated reducer fastener ring 23 consists of a flexible plastic material formed in a generally circular design. Other shapes and materials may also be used for the fastener ring depending upon the exterior configuration of the cannula with which it is intended to be used. The fastener ring 23 also contains a removal tab 24 which allows for easy removal of the reducer system 21 from the end cap 41. The interior diameter of the fastener ring 23 is slightly smaller than the exterior of the second raised edge 43 near the proximate end of the end cap 41. Second raised edge 43 thereby forms a fastening groove. The fastener ring 23 may be removably attached to the end cap 41 by sliding ring 23 over the second raised edge 43 near the proximate end of the cannula end cap 41 into fastening groove 45 thereby locking it into place and securing the reducer system 21 to the cannula 12. After the reducer system 21 is no longer needed, it may be removed by pulling up on the fastener ring removal tab 24 and thereby sliding the fastener ring 23 over the raised edges 43, 44 at the proximate end of the end cap 41.

The fastener ring 23 is pivotably connected to the reducer cap 29, which contains the gasket assembly 31, preferably by a living hinge 22 as shown in FIGS. 2 and 4. The living hinge 22 consists of the same flexible hardened material as the fastener ring 23 and the reducer cap 29 containing the gasket assembly 31. The living hinge 22 connects the fastener ring 23 and the reducer cap 29 containing the gasket assembly 31 while acting as a hinge. The living hinge 22 consists of a thin sheet of material with a fold in the middle which allows one to either fasten the reducer cap 29 into place onto the end cap 41 over aperture 51 or leave the reducer cap 29 open and away from aperture 51.

As shown in FIGS. 2 and 4, the reducer cap 29 contains a locking mechanism 25, or latch, and an activator tab 28 which are used to lock the reducer cap 29 into place. The J-shaped locking mechanism 25 is made of a flexible material, preferably the same as the remainder of the reducer system 21. When activated in its closed position over aperture 51, the locking mechanism 25 mateably attaches to the first raised edge 44 at the proximate end of the end cap 41 and locks the reducer cap 29 into place. To either activate (close) or deactivate (open) the reducer cap 29, the activator tab 28 is used. The activator tab 28 is designed so that the cap can either be activated or deactivated easily with the use of a finger.

The reducer cap 29 contains the outer gasket assembly housing 26 as shown in FIG. 2. The outer gasket assembly housing 26 contains a reduced diameter opening 52 on the top of the reducer cap. Located on the inside of the outer gasket assembly housing 26 is a ridge, not visible in the illustration, which mateably interacts with the raised edge 35 located in the middle of the reducer cap gasket member 37. Also, the diameter of the reducer cap gasket assembly interface 27 is slightly smaller than that of the cannula end cap 41 so the gasket assembly interface 27 lies flush with the inside of the aperture 51 of end cap 41.

Figure 5A:
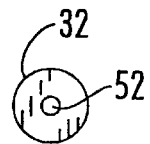
FIG. 5A is a top view of the reducer cap wiper seal of FIG. 4 shown in isolation.
Figure 5B:
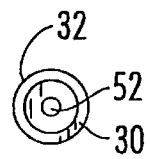
FIG. 5B is a bottom view of the reducer cap wiper seal shown of FIG. 4 shown in isolation.
Figure 5C:
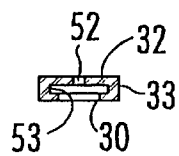
FIG. 5C is a cross sectional view of the reducer cap wiper seal of FIG. 4 shown in isolation.
Figure 6:
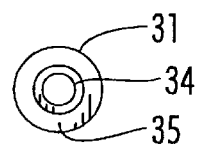
FIG. 6 is a top view of the gasket of the reducer cap gasket assembly of FIG. 4 shown in isolation.

Finally, the gasket assembly is shown in FIGS. 2, 5, and 6. The reducer cap gasket seal system contains two components. The first component is the reducer cap wiper seal 32 shown in FIGS. 2, 4, and 5. The reducer cap wiper seal 32 is fabricated from a material which has sufficient elasticity so that the edge 30 of the seal 32 can be stretched over the proximate raised edge 34 and thereby mounted on the gasket 37. The proximate raised edge 34 of the gasket fits within a channel 53 formed by the C-shaped edge 33 of the reducer cap wiper seal 32 as shown in FIGS. 5B and 5C. The wiper seal 32 contains the reduced opening 52 which reduces the cannula's effective diameter while maintaining pneumoperitoneum.

The second component of the gasket assembly 31 is the gasket member 37 as is shown in FIGS. 2 and 6. The gasket 37 contains the proximate raised edge 34 used to mateably attach the reducer cap wiper seal 32, the raised edge 35 used to lock the gasket seal system 37, 32 into the outer gasket assembly housing 26, and the distal conical shaped cylinder 36 which creates a seal between the reducer cap 29 and the wiper seal 42 in cannula end cap 41. The gasket 37 is preferably constructed of a durable, rigid plastic material. The distal conical shape cylinder 36 is designed so that when the reducer cap 29 is placed in its closed and latched position, pneumoperitoneum will be maintained. The lower diameter of the conical shaped cylinder 36 is smaller than the upper diameter of the cylinder. When the reducer cap 29 is locked into place, the bottom of the conical shaped cylinder 36 extends through the opening 50 in the end cap wiper seal 42. The upper diameter of the conical shaped cylinder 36 is larger than the opening 50 of the end cap wiper seal 42 and does not extend through that opening 51. Thus, when the reducer cap 29 is locked into place onto the end cap 41, an air-tight seal is achieved between the conical shaped cylinder 36 and the end cap wiper seal 42. In the illustration of the FIGS. 1A and 2, wiper seal 42 is mounted on gland retainer 56 within the handle of cannula 12. Another seal, flapper valve 57 is also illustrated and effectively maintains pneumoperitoneum when no surgical instruments are inserted through the lumen 14 of the cannula 12.

A great advantage of the present reducer system 21 is that the fastener ring 23 can be attached to cannula end cap 41 prior to surgery. This is achieved by having the fastener attach to mounting points such as fastening grooves 45 that are on the exterior of the cannula 12. The reducer system 21 can be left in its open position and an obturator 11 can be inserted through the opening 52 in end cap 41 down the lumen 14 of the cannula 12. After the obturator 11 and cannula 12 have been used to make an incision, the obturator 11 is removed. Then the cannula can either be used with an endoscopic instrument of diameter similar to the obturator 11, or the reducer cap 29 can be latched in its closed position and an endoscopic instrument of smaller diameter deployed. By fixing the reducer system 21 in place prior to surgery, there is no need to locate and select the appropriate reducer in the middle of a surgical procedure.

Numerous alterations of the structures herein described will suggest themselves to those skilled in the art. It is to be understood that the details and arrangements of the parts that have been described and illustrated in order to explain the nature of the invention are not to be construed as any limitation of the invention. All such alterations which do not depart from the spirit of the invention are intended to be included within the scope of the appended claims.

We claim:

1. A trocar reducer system comprising:
   (a) a cannula having a distal end and a proximate end, and further having an interior lumen and an exterior surface;
   (b) a reducer system having a fastener attached to the exterior surface of the proximate end of said cannula, and a reducer cap pivotally connected to said fastener thereby permitting said reducer cap to pivotally move between an activated position closed over said cannula lumen and a deactivated position;

wherein the proximate end of the cannula comprises an end section having at least one raised edge with an exterior surface and the reducer system fastener comprises a fastening ring having a smaller inner dimension than the exterior surface of said at least one raised edge; and wherein the reducer cap further comprises a latching means which engages a raised edge of the end section of the cannula when the reducer cap is closed over the cannula lumen.

2. The trocar reducer system of claim 1 wherein the reducer cap further comprises an activator tab for engaging and disengaging the latching means.

3. The trocar reducer system of claim 1 wherein the fastening ring further comprises a removal tab for engaging and disengaging the fastening ring from the raised edge.

4. The trocar reducer system of claim 1 wherein the reducer cap further comprises a gasket assembly housing.

5. The trocar reducer system of claim 4 wherein the gasket assembly housing, latching means, and fastening ring are formed from a unitary piece of material.

6. The trocar reducer system of claim 4 wherein a gasket member is provided with a proximal portion to engage the gasket assembly housing and a distal conical portion.

7. The trocar reducer system of claim 6 wherein the proximate end of the cannula comprises a seal having an opening which is filled by the distal conical portion of the gasket member of the reducer cap when the reducer cap is in its activated closed position.

8. A trocar reducer system comprising:
   (a) a cannula having a distal end and a proximate end, and further having an interior lumen and an exterior surface;
   (b) a reducer system having a fastener attached to the exterior surface of the proximate end of said cannula, and a reducer cap pivotally connected to said fastener thereby permitting said reducer cap to pivotally move between an activated position closed over said cannula lumen and a deactivated position;

wherein the proximate end of the cannula comprises an end section having at least one raised edge with an exterior surface and the reducer system fastener comprises a fastening ring having a smaller inner dimension than the exterior surface of said at least one raised edge; and wherein the end section has at least a first distal raised edge and a second proximate raised edge and the inner dimension of the fastening ring is smaller than the exterior surface of the first distal raised edge.

9. The trocar reducer system of claim 8 wherein the reducer cap further comprises a latch which engages the second proximate raised edge.

10. The trocar reducer system of claim 9 wherein the fastening ring further comprises a removal tab for engaging and disengaging the fastening ring from the first distal raised edge.

11. The trocar reducer system of claim 8 wherein the reducer cap further comprises an activator tab for engaging and disengaging the latch.

12. A trocar reducer system comprising:
   a) a cannula having a distal end and a proximate end, and having an interior lumen and an exterior surface;
   b) the proximal end of said cannula having an end section with an aperture opening into the lumen, wherein a wiper seal is seated within said end section, and said end section has a first distal raised edge with an exterior surface and a second proximate raised edge;
   c) a fastening ring having a smaller inner dimension than the exterior surface of the first raised edge and mounted distal of said first edge;
   d) said fastening ring being connected by a living hinge to a reducer cap, wherein the reducer cap further comprises a gasket assembly housing and a gasket seal assembly, and said fastening ring, living hinge, and gasket assembly housing are formed from a unitary piece of material;

(e) said reducer cap further having a latch means that engages the second proximate raised edge of the end section when the reducer cap is closed over the aperture of the end section of the cannula.

13. The trocar reducer system of claim 12 wherein the gasket seal assembly comprises a wiper seal.

14. The trocar reducer system of claim 12 wherein the gasket seal assembly comprises a gasket member.

15. The trocar reducer system of claim 14 wherein the gasket member comprises a proximate portion for interfacing with a wiper seal, an intermediate portion to engage the gasket assembly housing, and a distal conical portion.

16. The trocar reducer system of claim 15 wherein the proximate end of the cannula comprises a seal having an opening which is filled by the distal conical portion of the gasket member of the reducer cap when the reducer cap is in its activated closed position.

* * * * *